United States Patent
Yang et al.

(10) Patent No.: US 11,547,363 B2
(45) Date of Patent: Jan. 10, 2023

(54) PHYSIOLOGICAL SENSOR DEVICE AND SYSTEM, AND CORRECTION METHOD

(71) Applicant: Industrial Technology Research Institute, Hsinchu (TW)

(72) Inventors: Ming-Huan Yang, Hsinchu (TW); Kuang-Ching Fan, Hsinchu County (TW); Yen-Ting Wu, Taoyuan (TW); Yi-Cheng Lu, Hsinchu (TW); Jui-Chang Chuang, Kaohsiung (TW)

(73) Assignee: Industrial Technology Research Institute, Hsinchu (TW)

( * ) Notice: Subject to any disclaimer, the term of this patent is extended or adjusted under 35 U.S.C. 154(b) by 1016 days.

(21) Appl. No.: 16/262,933

(22) Filed: Jan. 31, 2019

(65) Prior Publication Data

US 2019/0246987 A1    Aug. 15, 2019

Related U.S. Application Data

(60) Provisional application No. 62/629,130, filed on Feb. 12, 2018.

(30) Foreign Application Priority Data

Aug. 28, 2018    (TW) ................................ 107129978

(51) Int. Cl.
*A61B 5/00* (2006.01)
*A61B 5/0205* (2006.01)
(Continued)

(52) U.S. Cl.
CPC .......... *A61B 5/721* (2013.01); *A61B 5/02055* (2013.01); *A61B 5/02405* (2013.01);
(Continued)

(58) Field of Classification Search
CPC ........... A61B 5/721; A61B 5/276; A61B 5/24; A61B 5/02055; A61B 5/02438;
(Continued)

(56) References Cited

U.S. PATENT DOCUMENTS 6,597,942 B1 *  7/2003  Yonce .................. A61B 5/6843
                                                      600/512
6,801,802 B2    10/2004  Sitzman et al.
(Continued)

FOREIGN PATENT DOCUMENTS

CN          1919139          2/2007
CN          1985751          6/2007
(Continued)

OTHER PUBLICATIONS

"Office Action of Taiwan Counterpart Application," dated Apr. 17, 2019, p. 1-p. 4.
(Continued)

*Primary Examiner* — Mallika D Fairchild
*Assistant Examiner* — Amanda L Steinberg
(74) *Attorney, Agent, or Firm* — JCIPRNET

(57) ABSTRACT

A physiological sensor device and system, and a correction method are provided. The physiological sensor device includes a physiological signal sensor, a first compensation sensor, and a signal processing device. The physiological signal sensor is attached to an object to be detected to sense a physiological signal value. The first compensation sensor is disposed on the physiological signal sensor. The signal processing device is coupled to the physiological signal sensor and the first compensation sensor. The signal processing device obtains through the first compensation sensor a failure region of the physiological signal sensor partially detached from the object to be detected and obtains a first failure compensation value according to the failure region, (Continued)

so as to compensate the physiological signal value sensed by the physiological signal sensor.

12 Claims, 15 Drawing Sheets

(51) Int. Cl.
  *A61B 5/024* (2006.01)
  *A61B 5/276* (2021.01)
  *A61B 5/24* (2021.01)
  *A61B 5/08* (2006.01)
  *A61B 5/30* (2021.01)
  *A61B 5/316* (2021.01)

(52) U.S. Cl.
  CPC ............ *A61B 5/02438* (2013.01); *A61B 5/24* (2021.01); *A61B 5/276* (2021.01); *A61B 5/688* (2013.01); *A61B 5/6833* (2013.01); *A61B 5/6843* (2013.01); *A61B 5/7203* (2013.01); *A61B 5/0002* (2013.01); *A61B 5/0205* (2013.01); *A61B 5/08* (2013.01); *A61B 5/30* (2021.01); *A61B 5/316* (2021.01); *A61B 5/743* (2013.01); *A61B 2562/164* (2013.01)

(58) Field of Classification Search
  CPC ..... A61B 5/6833; A61B 5/6843; A61B 5/688; A61B 5/7203; A61B 5/30; A61B 5/0002; A61B 5/0205; A61B 5/08; A61B 5/743
  See application file for complete search history.

(56) References Cited

U.S. PATENT DOCUMENTS

| | | |
|---|---|---|
| 8,814,792 B2 | 8/2014 | Raptis et al. |
| 8,965,479 B2 | 2/2015 | Wilder-Smith et al. |
| 9,295,424 B2 | 3/2016 | Todorov et al. |
| 9,462,979 B2 | 10/2016 | Lisogurski et al. |
| 10,898,094 B1 | 1/2021 | Lisy et al. |
| 2001/0027270 A1* | 10/2001 | Stratbucker ............ A61B 5/259 600/382 |
| 2006/0085049 A1* | 4/2006 | Cory .................... A61B 5/4041 607/48 |
| 2014/0206977 A1 | 7/2014 | Bahney et al. |
| 2014/0296934 A1* | 10/2014 | Gozani ................ A61B 5/0531 607/46 |
| 2015/0164324 A1 | 6/2015 | Russell |
| 2016/0206243 A1 | 7/2016 | Pang et al. |
| 2017/0020459 A1 | 1/2017 | Al Hatib |
| 2017/0071491 A1 | 3/2017 | Litt et al. |

FOREIGN PATENT DOCUMENTS

| | | |
|---|---|---|
| CN | 101547635 | 9/2009 |
| CN | 102113884 | 7/2011 |
| CN | 105377359 | 3/2016 |
| CN | 107224281 | 10/2017 |
| CN | 107320095 | 11/2017 |
| CN | 107495929 | 12/2017 |
| CN | 107536607 | 1/2018 |
| EP | 1575424 | 9/2005 |
| TW | 200829208 | 7/2008 |
| TW | 201542161 | 11/2015 |
| TW | I568411 | 2/2017 |
| TW | I581195 | 5/2017 |
| TW | I598073 | 9/2017 |

OTHER PUBLICATIONS

"Notice of Allowance of Taiwan Related Application, application No. 107129561", dated Mar. 15, 2019, p. 1-p. 4.
"Office Action of China Counterpart Application", dated Jun. 28, 2021, p. 1-p. 9.
"Office Action of China Related Application No. 201810972251.4", dated Jun. 28, 2021, pp. 1-10.

* cited by examiner

PHYSIOLOGICAL SENSOR DEVICE AND SYSTEM, AND CORRECTION METHOD

CROSS REFERENCE TO RELATED APPLICATION

This application claims the priority benefit of U.S. provisional application Ser. No. 62/629,130, filed on Feb. 12, 2018 and Taiwan application serial no. 107129978, filed on Aug. 28, 2018. The entirety of each of the above-mentioned patent applications is hereby incorporated by reference herein.

TECHNICAL FIELD

The disclosure relates to a signal detection and processing technology, the disclosure also relates to a physiological sensor device, a physiological sensor system, and a correction method of a physiological signal.

BACKGROUND

According to a biomedical detection technology applied to a wearable device, physiological signal detection equipment (e.g., a sensing electrode pad or a sensor) may be worn by a wearer, and various physiological signals of the wearer are recorded at any time in a non-invasive manner, so as to detect the body temperature, the pulse, the heart rate, the respiratory rate, and other physiological conditions of the wearer. Moreover, the wearer may be reminded of and protected from possible physiological abnormalities; even when symptoms occur, the physiological signal detection equipment can achieve the effect of promptly reminding the wearer and asking for help. Hence, the wearable biomedical detection technology is extremely convenient for wearers such as patients at home, patients with a history of heart disease, or elderly who live alone.

However, due to the limitations of the related art, the sensing electrode pad required to be closely attached to the skin of the wearer is often warped, falls off from the wearer, etc., and therefore improvement of user's experience may still be required. Specifically, the conventional physiological signal detection equipment (e.g., the sensing electrode pad or the sensor) is usually required to be in close contact with the skin of the wearer for obtaining an accurate physiological signal; however, due to the sweat on the skin of the wearer, the pulling force generated by the wearer's behavior, or other factors, the sensing electrode pad may be completely or partially fall off or may not be closely attached to the skin of the wearer, thus resulting in distortion of the detected physiological signal. In the related art, the solutions generally involve enhancement of the adhesiveness of the sensual electrode patch to enhance the adhesion to the skin. However, in such solutions, the wearer is generally more uncomfortable, fall-off is still possible, or the arrangement of the sensing electrode patch is more inconvenient. Moreover, in many cases, the wearer is not aware that the sensing electrode pad has fallen off, thus leading to distortion and poor accuracy of the physiological signal.

SUMMARY

An embodiment of the disclosure provides a physiological sensor device including a physiological signal sensor, a first compensation sensor, and a signal processing device. The physiological signal sensor is attached to an object to be detected to sense a physiological signal value. The first compensation sensor is disposed on the physiological signal sensor. The signal processing device is coupled to the physiological signal sensor and the first compensation sensor. The signal processing device obtains through the first compensation sensor a failure region of the physiological signal sensor partially detached from the object to be detected and obtains a first failure compensation value according to the failure region, so as to compensate the physiological signal value sensed by the physiological signal sensor.

A physiological signal correction method of an embodiment of the disclosure adapted to a physiological sensor device includes a physiological signal sensor and a first compensation sensor. The first compensation sensor is disposed on the physiological signal sensor. The correction method includes following steps: in response to the physiological signal sensor attached to an object to be detected, obtaining a physiological signal value from the physiological signal sensor; obtaining through the first compensation sensor a failure region of the physiological signal sensor partially detached from the object to be detected; obtaining a first failure compensation value according to the failure region, so as to compensate the physiological signal value sensed by the physiological signal sensor.

An embodiment of the disclosure provides a physiological sensor system including a host device and a physiological sensor device. The host device and the physiological sensor device communicate with each other. The host device obtains a compensated physiological signal value provided by the physiological sensor device to perform data computation and presents a physiological signal value after the data computation. The physiological sensor device includes a physiological signal sensor, a first compensation sensor, and a signal processing device. The physiological signal sensor is attached to an object to be detected to sense a physiological signal value. The first compensation sensor is disposed on the physiological signal sensor. The signal processing device is coupled to the physiological signal sensor and the first compensation sensor. The signal processing device obtains through the first compensation sensor a failure region of the physiological signal sensor partially detached from the object to be detected and obtains a first failure compensation value according to the failure region, so as to compensate the physiological signal value sensed by the physiological signal sensor.

The foregoing will become better understood from a careful reading of a detailed description provided herein below with appropriate reference to the accompanying drawings.

DETAILED DESCRIPTION OF EMBODIMENTS

Figure 1:
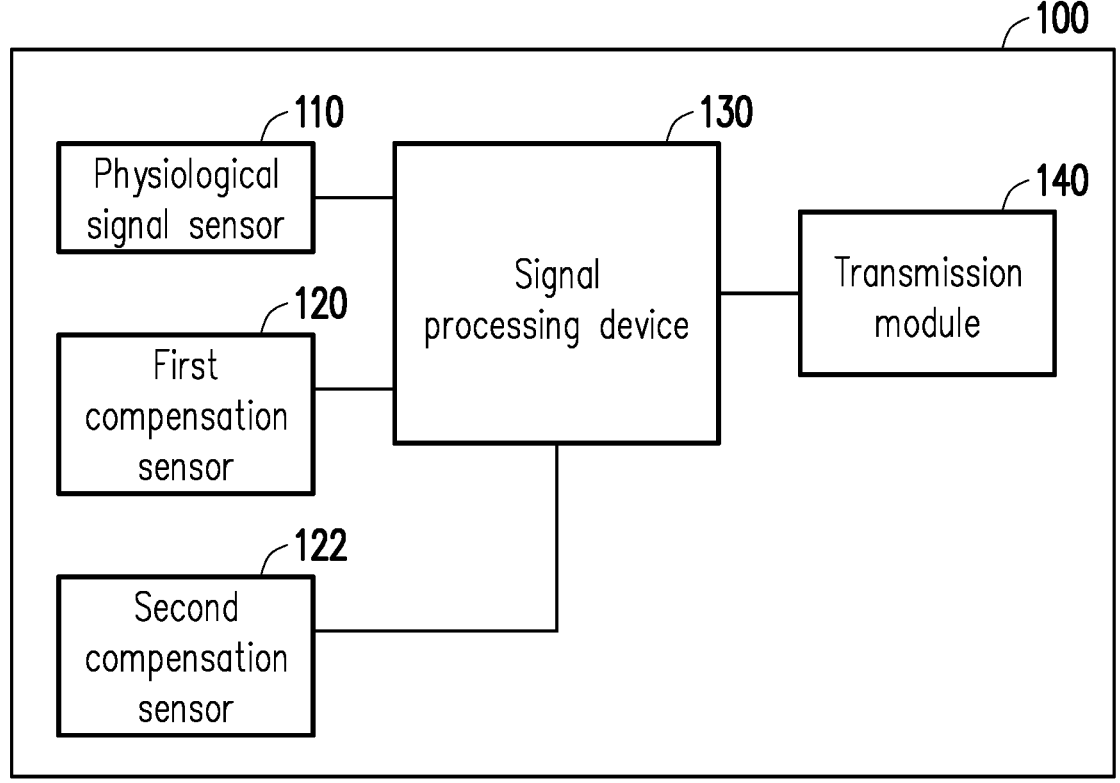
FIG. 1 is a block diagram of a physiological sensor device according to an embodiment of the disclosure.

In order to make the disclosure more comprehensible, embodiments are described below as the examples to prove that the disclosure can actually be realized. In addition, wherever possible, elements/components/steps denoted by the same reference numerals in drawings and embodiments represent the same or similar parts.

Figure 2:
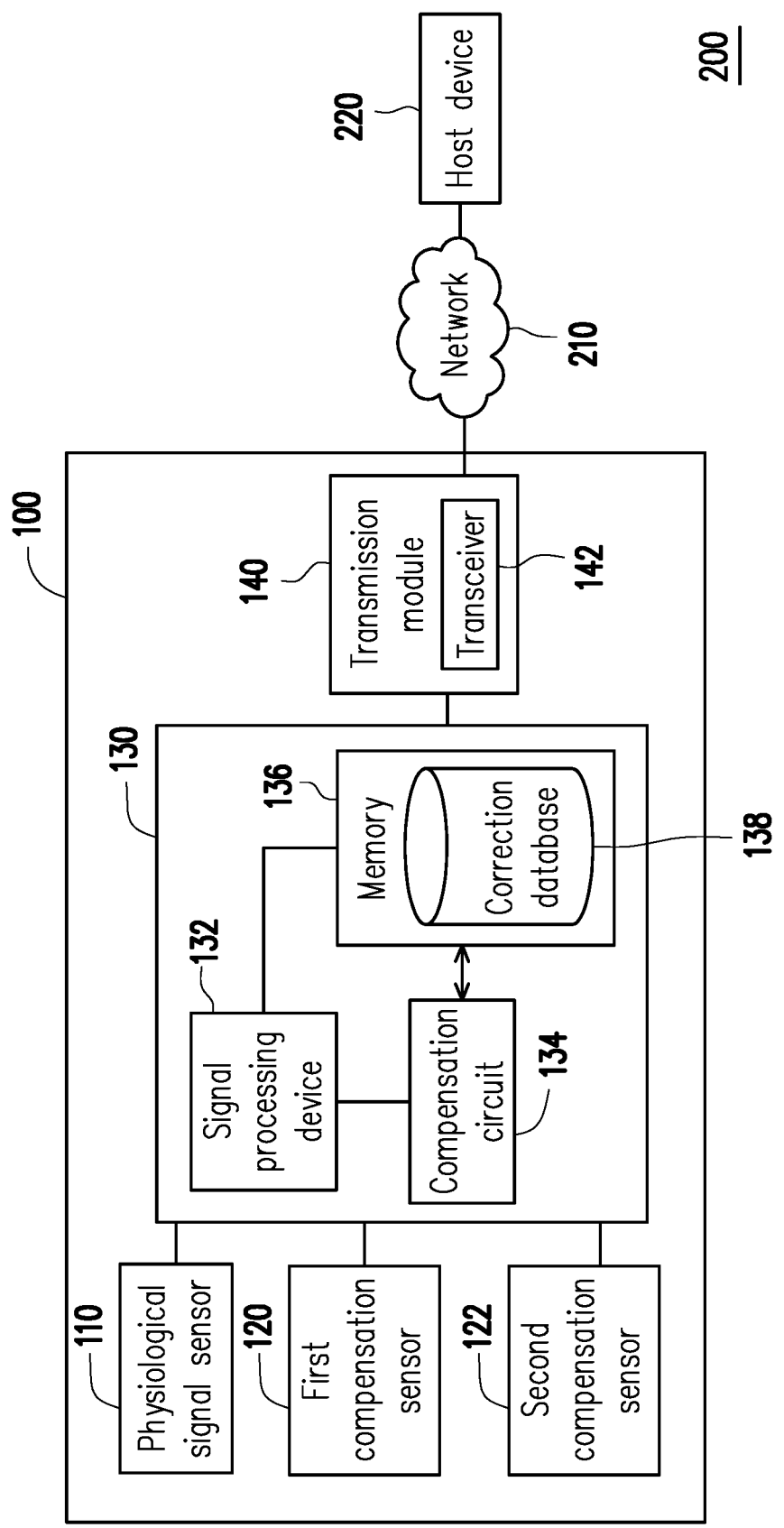
FIG. 2 is a block diagram of a physiological sensor system according to an embodiment of the disclosure.

FIG. 1 is a block diagram of a physiological sensor device 100 according to an embodiment of the disclosure. FIG. 2 is a block diagram of a physiological sensor system 200 according to an embodiment of the disclosure. With reference to FIG. 1 and FIG. 2, a physiological sensor system 200 includes a physiological sensor device 100 and a host device 220. The physiological sensor device 100 may communicate with the host device 220 through a transmission module 140, cable or wireless network 210, and relevant transmission protocols (e.g., Bluetooth, WIFI, etc.). The physiological sensor device 100 provides a compensated physiological signal value to the host device 220. After the host device 220 obtains the physiological signal value, the host device 220 may perform data computation and present the physiological signal value after the data computation. For instance, the host device 220 may present the physiological signal value on a display of the host device 220 in form of tables, images, and/or specific user interfaces, so that a user is able to learn the value of his/her physiological signals and the variations thereof. In the embodiment, the host device 220 may be a consumer computing device (e.g., a notebook computer, a tablet, or a smart phone) or a cloud server (also referred to as a cloud computing platform). That is, the host device 220 mainly serves to present the physiological signal values of the wearer (e.g., the body temperature, the pulse, the heart rate, the respiratory rate, and the dynamic myoelectric current value), also display the integrated or corrected physiological conditions or physiological information (e.g., muscle endurance, muscle strength, muscle fatigue, physical condition, exercise cycle, health condition, abnormal warnings) on the display.

The physiological sensor device 100 includes a physiological signal sensor 110, a first compensation sensor 120, and a signal processing device 130. The physiological sensor device 100 may include the transmission module 140 and a second compensation sensor 122. The physiological signal sensor 110 is equipped with one or more sensing electrodes. The physiological signal sensor 110 is attached to an object to be detected to obtain the physiological signal value from the sensing electrode. The "physiological signal" provided in the embodiment may be a body temperature, a pulse, a heart rate, a respiratory rate, a dynamic myoelectric current value, an electroencephalography (EEG), an electromyography (EMG), an electroneurogram (ENG), an electroretinogram (ERG), an electrogastrogram (EGG), an electroneuromyography (ENMG), an electrocorticography (ECoG), an electrooculogram (EOG), an electronystagmography (ENG), etc., and the type of the physiological signal detected by the physiological signal sensor 110 is determined according to the usage and the requirements of the physiological sensor device 100. In the embodiment, the "physiological signal value" is the value of the physiological signal of the types above. In the embodiment, the "object to be detected" is mainly the skin of a user (or referred to as a wearer, e.g., a person or an animal), and a person implementing the embodiment may also regard another object as the object to be detected as long as the physiological signal value can be sensed from the object to be detected. The first compensation sensor 120 is disposed on the physiological signal sensor 110. The physiological signal sensor 110 and the first compensation sensor 120 may be made of shapeable or flexible material.

The first compensation sensor 120 is equipped with a plurality of first compensation electrodes. In the embodiment, the first compensation electrodes are disposed on the edge of a sensing region formed by the sensing electrode in the physiological signal sensor 110, so that the signal processing device 130 is able to detect whether the sensing region is partially detached from the object to be detected (skin). If the physiological signal sensor 110 is detached from the object to be detected, a partial region (e.g., a corner region) is presumed to be detached from the object to be detected, so that some of the first compensation electrodes cannot be connected to the object to be detected, while the other first compensation electrodes are still connected to the object to be detected. In other words, when some of the first compensation electrodes are not connected to the object to be detected, the first compensation signal generated by these first compensation electrodes is different from the first compensation signal generated by the first compensation electrodes that are still connected to the object to be detected. Thereby, the signal processing device 130 is able to learn a plurality of failure locations between the first compensation electrodes not connected to the object to be detected and the first compensation electrodes connected to the object to be detected and calculate an area of a failure region according to the failure locations in a geometric mathematical operation.

The signal processing device 130 is coupled to the physiological signal sensor 110 and the first compensation sensor 120. The signal processing device 130 obtains through the first compensation sensor 120 the failure region of the physiological signal sensor 110 partially detached from the object to be detected and obtains a first failure compensation value according to the failure region. Thereby, the signal processing device 130 may compensate the physiological signal value sensed by the physiological signal sensor 110 according to the first failure compensation value.

The signal processing device 130 may include a processor 132, a compensation circuit 134, and a memory 136. The compensation circuit 134 is coupled to the processor 132. The memory 136 is simultaneously coupled to the processor 132 and the compensation circuit 134. The memory 136 includes a correction database 138. The correction database 138 at least includes correction information and relevant parameters corresponding to a compensation data generated by the physiological signal sensor 110, the first compensation sensor 120, and the second compensation sensor 122. In the embodiment, the processor 132 may communicate with the host device 220 through a transceiver 142 in the transmission module 140 and may update the content of the correction database 138 through the host device 220, so as to more accurately correct the physiological signal value. The following embodiments are provided for further explanation.

Figure 3A:
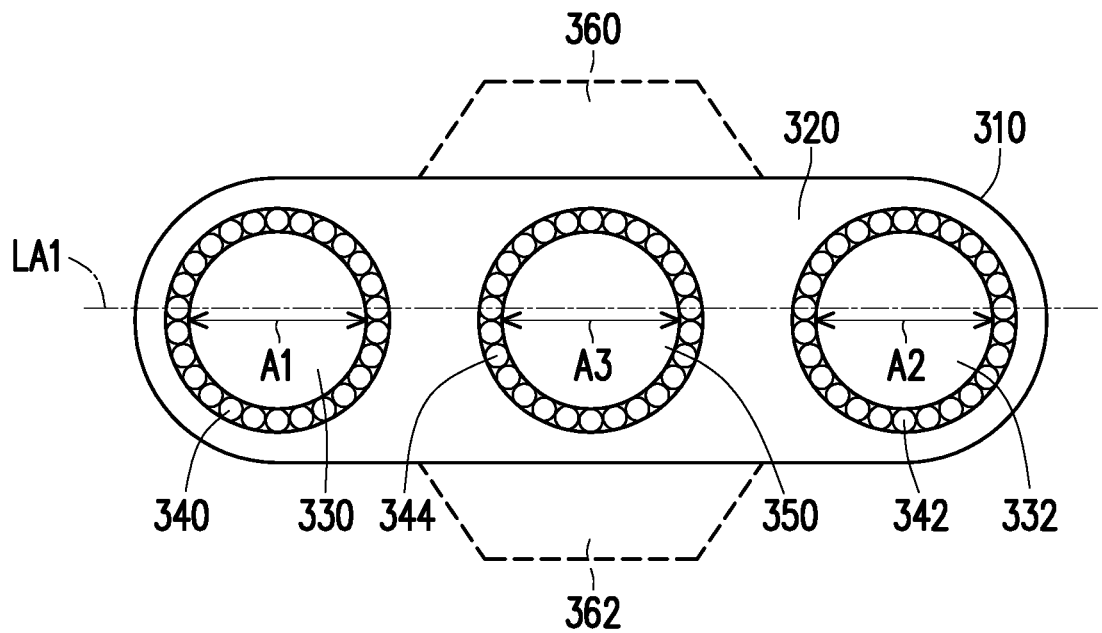
FIG. 3A and FIG. 3B are schematic diagrams illustrating an appearance of a physiological sensor device according to an embodiment of the disclosure.
Figure 3B:
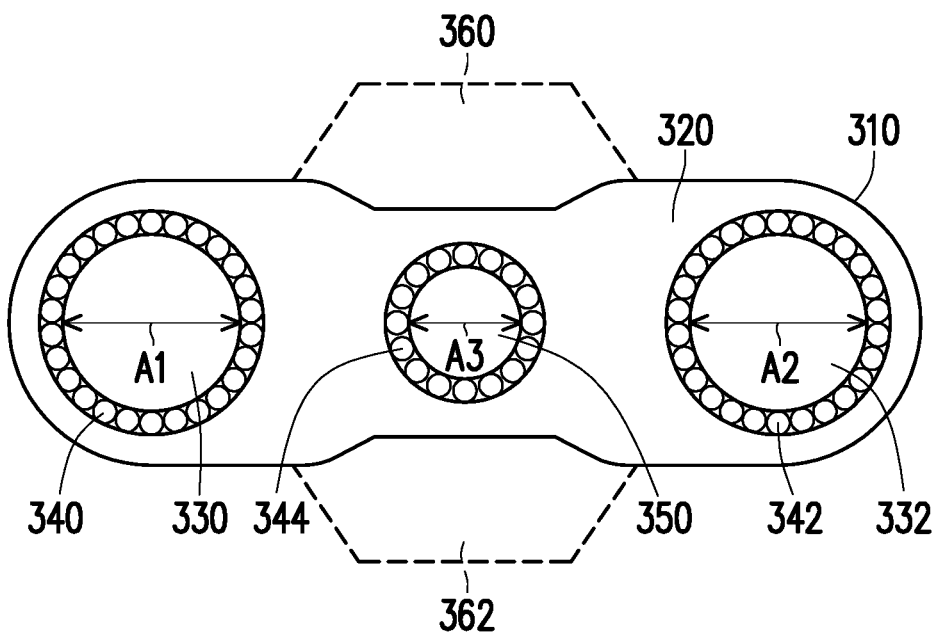

FIG. 3A and FIG. 3B are schematic diagrams illustrating an appearance of a physiological sensor device according to an embodiment of the disclosure. The physiological sensor device 100A depicted in FIG. 3A and the physiological sensor device 100B depicted in FIG. 3B are presented in form of a flexible patch and include a casing 310, an adhesive layer 320, sensing regions 330 and 332, compensation electrodes 340, 342, and 344, and a reference electrode 350. The physiological sensor device 100 may optionally include side adhesion regions 360 and 362.

The casing 310 may be implemented in form of a flexible material. The adhesive layer 320 allows the physiological sensor device 100 to be attached to the object to be detected (skin). The sensing regions 330 and 332 are surrounded by a plurality of compensation electrodes in the physiological signal sensor 110. The sensing regions 330 and 332 and the reference electrode 350 provided in the embodiment are all circular, and people who apply the embodiment may also adjust the sensing regions 330 and 332 to be rectangular, elliptical, trapezoidal, in other geometric shapes, or in a shape of a combination of the shapes. In FIG. 3A, a diameter A1 of the sensing region 330, a diameter A2 of the sensing region 332, and a diameter A3 of the reference electrode 350 are the same. By contrast, in FIG. 3B, the diameter A1 of the sensing region 330 is the same as the diameter A2 of the sensing region 332, while the diameter A3 of the reference electrode 350 is shorter than the diameters A1 and A2. People who apply the embodiment may adjust the contact areas and the number of the sensing regions and the reference electrode based on requirements, and the contact areas are in contact with the object to be detected (skin). Some embodiments of the disclosure may have three or more sensing regions, or only one sensing region; a plurality of reference electrodes may be provided or no reference electrode may be configured.

The physiological sensor device 100 not only includes the sensing electrode and the compensation electrodes but also includes the reference electrode 350. The reference electrode 350 serves as a determination basis while the sensing electrode is being initialized, and the initial value sensed by the reference electrode may serve as a comparison reference of the value of the sensing electrode. That is, the reference electrode acting as the sensing electrode serves to calibrate the voltage level. The compensation electrodes 340, 342, and 344 are respectively disposed on the edge of the sensing region 330, the sensing region 332, and the reference electrode 350, so that the signal processing device 130 is able to learn through the compensation electrodes 340, 342, and 344 whether any portion of the sensing region 330, the sensing region 332, and the reference electrode 350 is detached from the object to be detected. An adhesive layer 320 may be distributed on the side adhesion regions 360 and 362 and is configured to enhance the adhesion between the physiological sensor device 100 and the object to be detected (e.g., skin). The side adhesion regions 360 and 362 may be composed of foam and adhesives, thus making the regions 360 and 362 less prone to be detached from the skin due to deformation and/or sweat.

Figure 4:
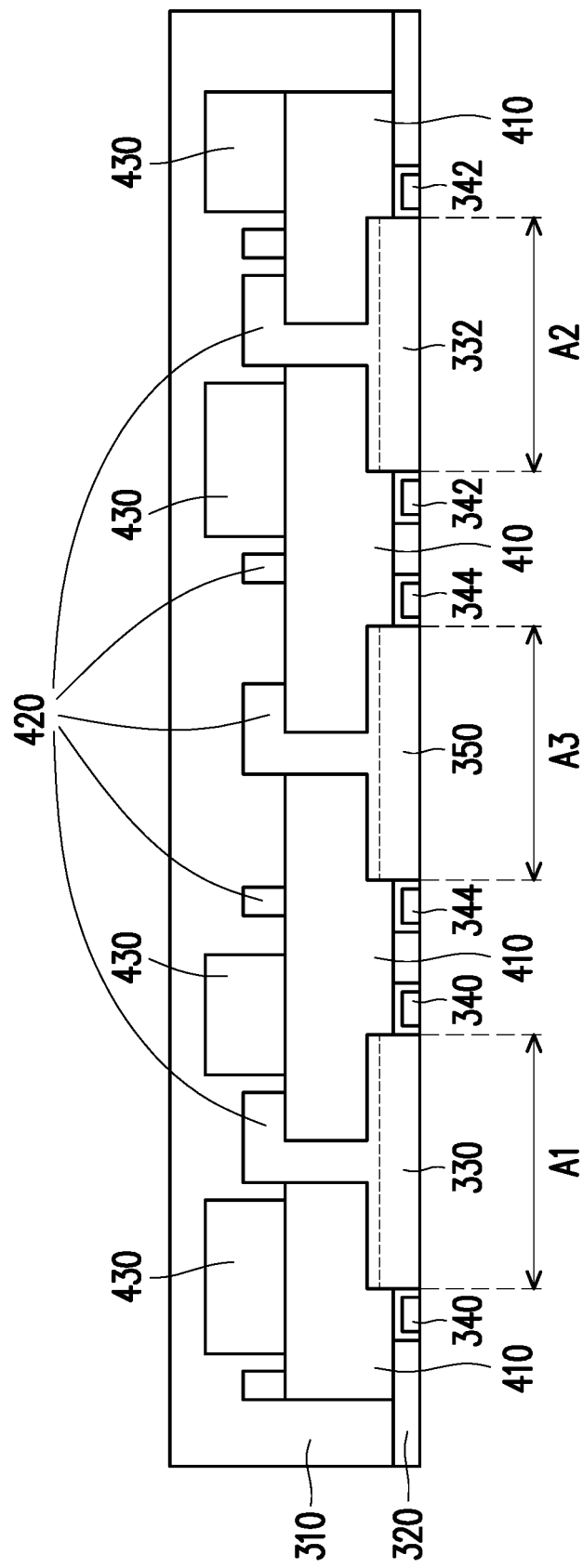
FIG. 4 is a schematic diagram illustrating a cross-section of the physiological sensor device depicted in FIG. 3A cut along a dividing line LA1.

FIG. 4 is a schematic diagram illustrating a cross-section of the physiological sensor device 100A depicted in FIG. 3A cut according to a dividing line LA1. The schematic cross-sectional view of FIG. 4 shows the relationship of the locations of the casing 310, the adhesive layer 320, the sensing regions 330 and 332 (a height of the sensing electrode constituting the sensing regions 330 and 332 is approximately 0.5 mm), the compensation electrodes 340, 342, and 344, and the reference electrode 350. In addition, FIG. 4 also depicts a flexible substrate 410 (with a height of approximately 100 µm to 200 µm), a circuit trace 420, and an integrated circuit 430 disposed on the flexible substrate 410 (with a height of approximately 2 µm to 5 µm). The integrated circuit 430 may be a device in the signal processing device 130 and the transmission module 140, e.g., a central processor, a memory device, a compensation circuit, etc.

The circuit trace 420 provided in the embodiment may be a conductive wire made of metallic copper. The sensing region 330 and 332 and the reference electrode 350 may be made of one or a combination of carbon glue, silver paste, silver chloride, copper, gold, or other conductive elements/compounds. The compensation electrodes 340, 342, and 344 may be surrounded by a thickened layer, and the thickened layer may be implemented by silica gel, resin, and other non-conductive fillers. According to the embodiment, the circuit trace 420 connected to the sensing regions 330 and 332 and the reference electrode 350 shown in FIG. 4 is implemented by the same manufacturing process and utilizing the same conductive element (e.g., copper); therefore, in between the sensing region 330 and the circuit trace 420, between the sensing region 332 and the circuit trace 420, and between the reference electrode 350 and the circuit trace 420 are shown in dotted lines. In other embodiments, the sensing regions 330 and 332 and the reference electrode 350 may be physically connected to the circuit trace 420 through soldering or punching, as long as the sensing regions 330 and 332 and the reference electrode 350 are electrically coupled to the corresponding circuit trace 420.

Figure 5:
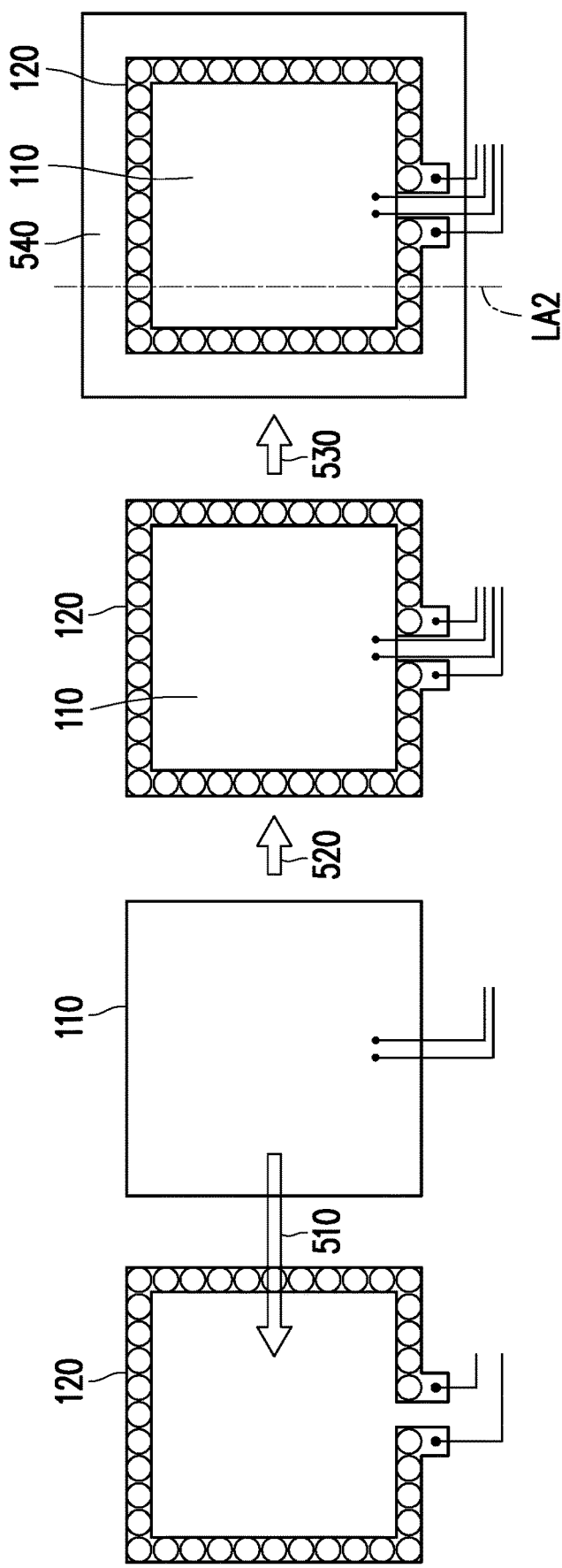
FIG. 5 is a schematic diagram of a physiological signal sensor, a first compensation sensor, and a fixing member.

FIG. 5 is a schematic view of the physiological signal sensor 110, the first compensation sensor 120, and a fixing member 540. In the embodiment, the physiological signal sensor 110 and the first compensation sensor 120 may be formed in different manufacturing processes, and then the physiological signal sensor 110 is combined (as indicated by arrow 510) with the first compensation sensor 120 and have both configured to the corresponding location (as indicated by arrow 520). Then, the relative physical relationship between the physiological signal sensor 110 and the first compensation sensor 120 is fixed (as indicated by arrow 530) by the fixing member 540 (e.g., a fixing pad) in a physical manner, so that the physiological signal sensor 110 and the first compensation sensor 120 are moved together, i.e., attached to or detached from the object to be detected together, so the embodiment of the disclosure may exert greater efficiency.

Figure 6A:
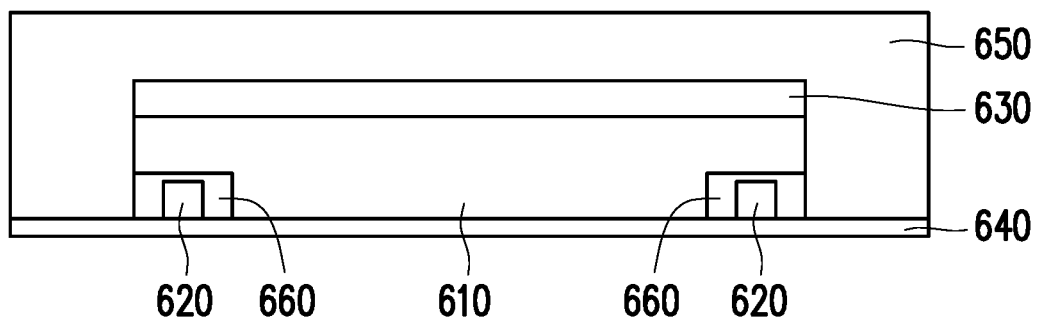
FIG. 6A and FIG. 6B are schematic diagrams illustrating in different manners a cross-section of the physiological signal sensor, the first compensation sensor and the fixing member depicted in FIG. 5 cut along a dividing line LA2.
Figure 6B:
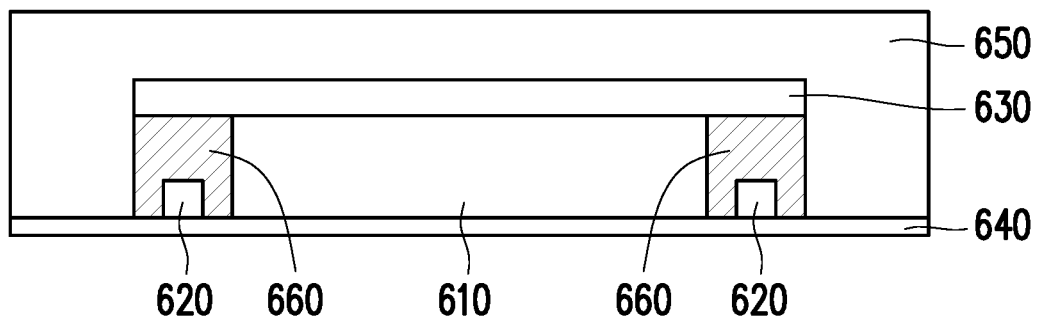

FIG. 6A and FIG. 6B are schematic views illustrating in different manners a cross-section of the physiological signal sensor 110, the first compensation sensor 120, and the fixing member 540 depicted in FIG. 5 cut along a dividing line LA2. In FIG. 6A and FIG. 6B, the fixing member 540 includes an optical adhesive layer 630, a polyurethane (PU) fixing adhesive layer 640, and a fixing layer 650. The optical adhesive layer 630 serves to closely adhere the fixing layer 650 to the physiological signal sensor 110. The PU fixing adhesive layer 640 acting as a carrier of the fixing layer 650, the physiological signal sensor 110, and the first compensation sensor 120, and also has adhesiveness. For instance, when the physiological signal sensor 110, the first compensation sensor 120, and the fixing member 540 receive a force and are thus bent, and a bending radius is about 30 mm, the compressive stress at the interface between the physiological signal sensor 110 and the PU fixing adhesive layer 640 is increased by 1.7%. Moreover, if adhesives (e.g., the optical adhesive layer 630 and the PU fixing layer 640) are fixed to both sides of the physiological signal sensor 110, the compressive stress at the interface is merely increased by 0.28%, so as to reduce the possibility of both the physiological signal sensor 110 and the first compensation sensor 120 falling off from each other. The greatest height of the fixing layer 650 may be 1.5 mm, and the height of the sensing electrode 610 may be 0.03 mm. An adhesive strength of the PU fixing adhesive layer 640 provided in the embodiment may be greater than 250 gf/25 mm. If the properties of the relevant adhesive material are limited to this range at the time of design, the issue of detachment of the physiological sensor device 100 in form of a pad from the skin may be avoided.

In FIG. 6A, each first compensation electrode 620 of the first compensation sensor 120 is disposed below the sensing electrode 610 of the first compensation sensor 120. The peripheries of the first compensation electrodes 620 are covered by a thickened layer 660. In FIG. 6B, each first compensation electrode 620 in the first compensation sensor 120 is disposed at the side of the sensing electrode 610 of the first compensation sensor 120; the thickened layer 660 not only serves to cover the peripheries of the first compensation electrodes 620 but is also used to fill the height difference between the first compensation electrodes 620 and the sensing electrode 610. The thickened layer 660 depicted in FIG. 6A and FIG. 6B may be implemented by non-conductive fillers such as silica gel and resin.

Figure 7A:
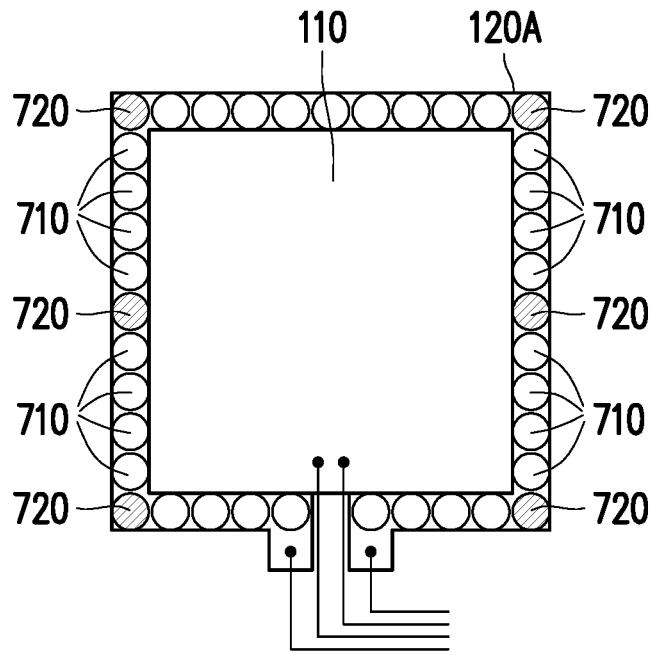
FIG. 7A and FIG. 7B are schematic diagrams illustrating a first compensation sensor in different manners respectively.
Figure 7B:
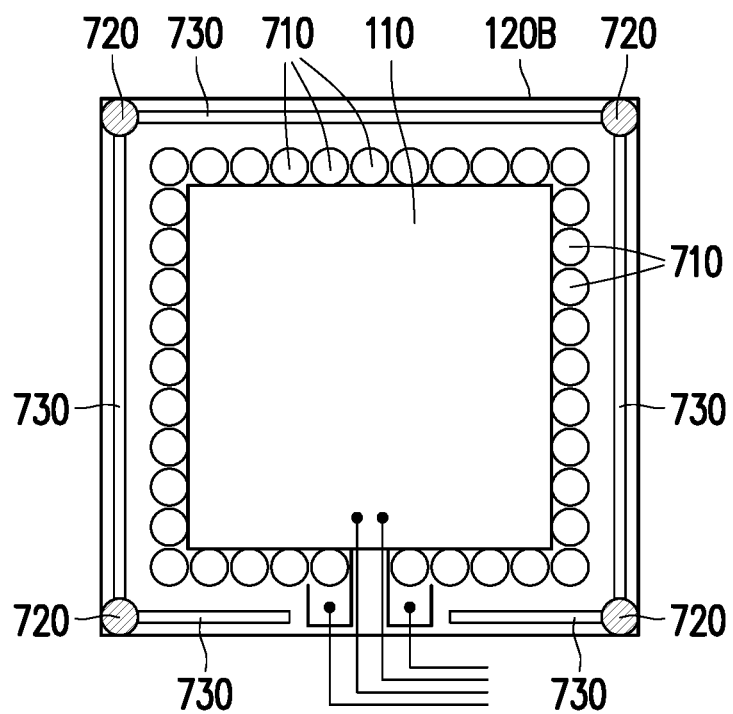

As shown in FIG. 3A, FIG. 3B, and FIG. 5, the first compensation electrodes (e.g., the compensation electrodes 340 and 342 shown in FIG. 3A and FIG. 3B) in the first compensation sensor 120 may be sensor devices of one single type or in one single form, e.g., a detachment sensor. The sensing devices of different types or in different forms may be used as the first compensation electrodes through design by people applying the embodiment. FIG. 7A and FIG. 7B are schematic diagrams illustrating a first compensation sensor 120A, 120B in different manners. In FIG. 7A, some of the first compensation electrodes (e.g., the compensation electrode 710) of the first compensation sensor 120A are the detachment sensors, while the other first compensation electrodes (e.g., the compensation electrode 720) may be replaced with other types of sensor devices, e.g., a sweat sensor, an acceleration sensor, an angular velocity sensor, and so on. In FIG. 7B, the first compensation sensor 120B not only includes the first compensation electrodes (e.g., the compensation electrode 710) but also adds other types of sensor devices as the first compensation electrodes. For instance, the compensation electrode 720 may be a sweat sensor, an acceleration sensor, an angular velocity sensor, a strain sensor, a temperature sensor, and so on, while the compensation electrode 730 may be a tensile sensor or a sensor in an elongated shape.

Figure 8A:
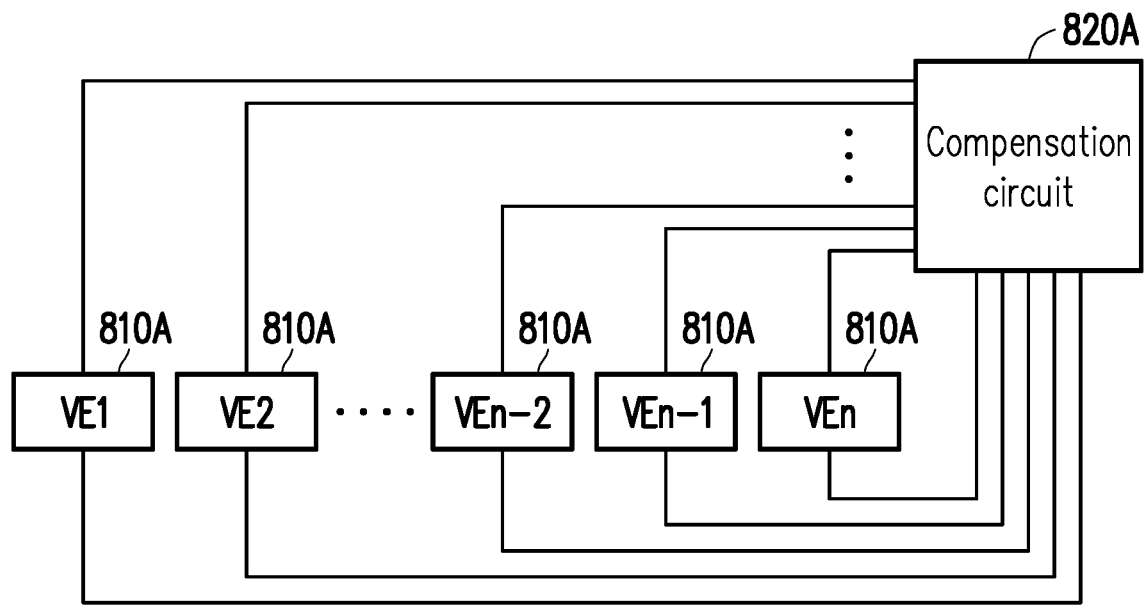
FIG. 8A and FIG. 8B are schematic diagrams of a first compensation sensor as a detachment sensor in form of resistors and capacitors.
Figure 8B:
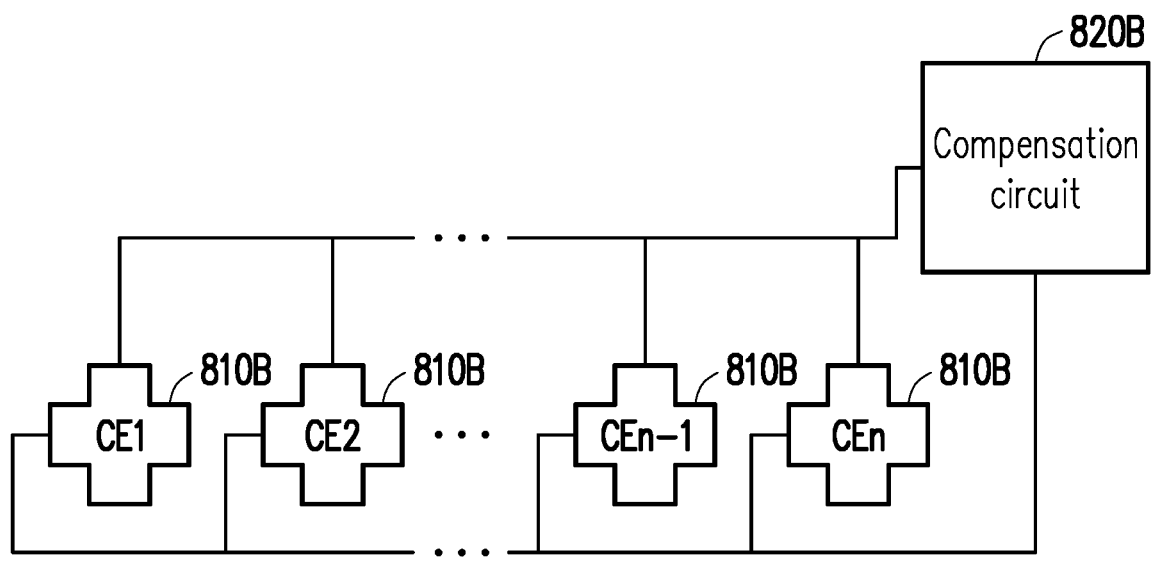

In the layout design of the first compensation sensor, the signal processing device may learn whether the first compensation electrodes are in contact with the skin with use of a plurality of first compensation electrodes in the first compensation sensor. FIG. 8A and FIG. 8B are schematic diagrams of a first compensation sensor as a detachment sensor in form of resistors and capacitors respectively. A plurality of first compensation electrodes 810A presented in FIG. 8A in form of resistors respectively each has resistances VE1 to VEn, and n is a natural number. The compensation circuit 820A located in the signal processing device may detect variations in the resistance of each first compensation electrode 810A to learn failure locations between the first compensation electrodes not connected to the object to be detected and the first compensation electrodes connected to the object to be detected, so as to perform calculations on the failure region. A plurality of first compensation electrodes 810B presented in FIG. 8B in form of capacitors respectively each has capacitances VC1 to VCn, and n is a natural number. The compensation circuit 820B located in the signal processing device may add the capacitances VC1 to VCn to obtain a total capacitance, so as to learn failure locations between the first compensation electrodes not connected to the object to be detected and the first compensation electrodes connected to the object to be detected and thereby perform calculations on the failure region.

Figure 9:
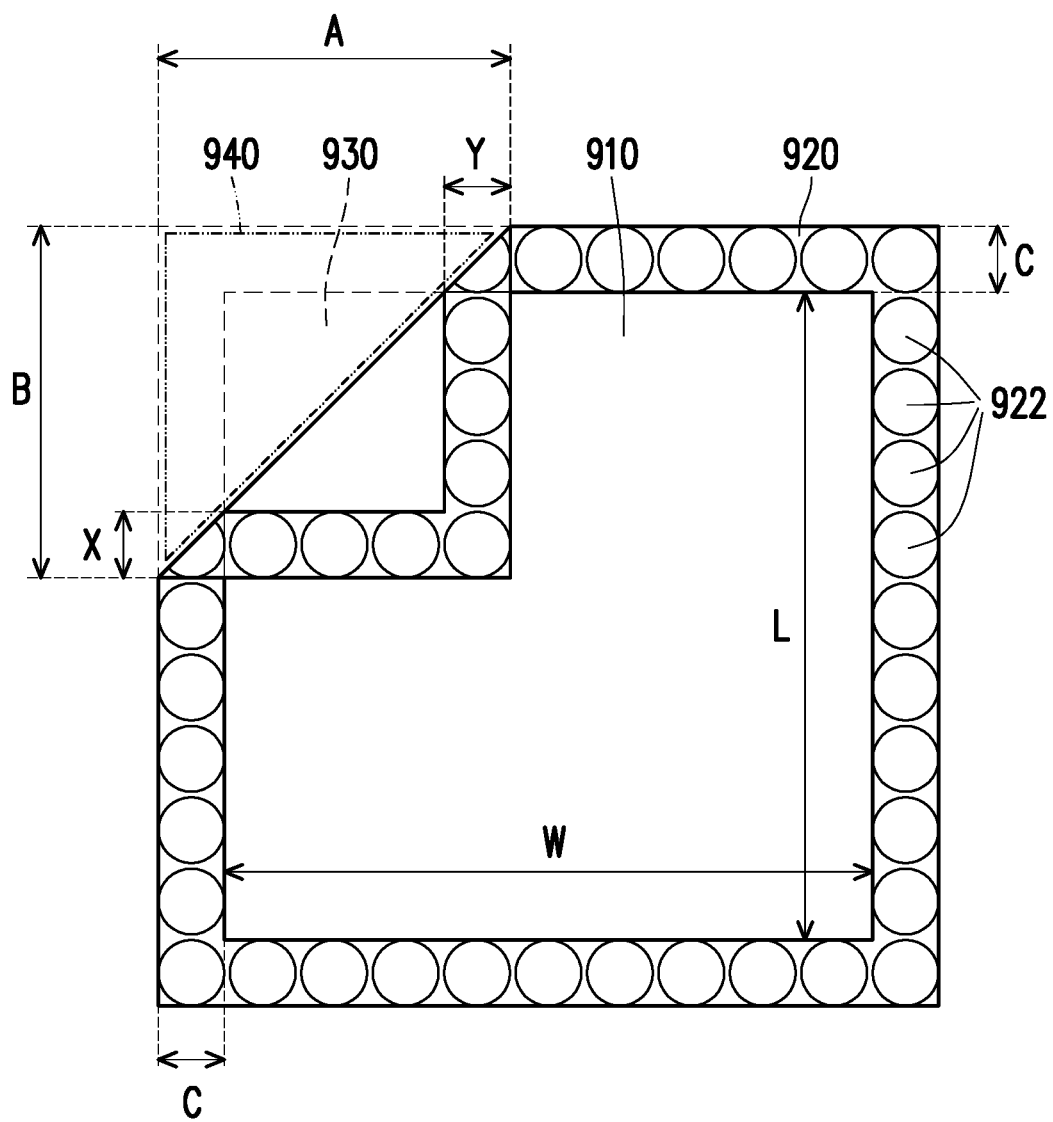
FIG. 9 is a schematic diagram of a sensing region and a failure region in a case where the sensing region is rectangular.

How to calculate the area of the failure region according to the geometric shape of the known sensing region in the physiological signal sensor and thereby compensate the physiological signal value is elaborated hereinafter. FIG. 9 is a schematic view of a sensing region 910 and a failure region, given that the sensing region 910 is rectangular. As shown in FIG. 9, the length and the width of the sensing region 910 of the rectangular shape are respectively represented by L and W, the first compensation region 920 is provided with a plurality of first compensation electrodes 922, and the width of the first compensation region 920 is set as C. When the pad-type physiological sensor device is partially detached, the detached portions of the sensing region 910 are often corner regions 930 and are collectively referred to as failure regions. In other words, the failure region is at least one corner region 930 detached from the object to be detected and located in the sensing region 910. When a plurality of corner regions are detached from the object to be detected, a total of the corner regions 930 is the failure region. For convenience of explanation, the embodiment of FIG. 9 is exemplified by a single corner region 930.

The signal processing device may obtain boundary lengths A and B and detachment lengths X and Y of the compensation region 940 including the failure region (e.g., the corner region 930) according to the first compensation electrodes not connected to the object to be detected and the first compensation electrodes connected to the object to be detected. A, B, C, X, Y, W, and L are all applied to indicate the length. As such, the signal processing device may calculate an area A930 of the failure region (i.e., the corner region 930) according to the boundary lengths A and B and calculate the first compensation value corresponding to the physiological signal value according to the area A930 and the area of the sensing region 910. Particularly, since the compensation region 940 and the corner region 930 should both be right-angled triangles of the same shape, the relationship between A, B, C, X, and Y can be expressed by equations (1) and (2):

$$\frac{C}{X} = \frac{A}{B} = \frac{Y}{C} \quad (1)$$

$$X = C \times \left(\frac{B}{A}\right); Y = C \times \left(\frac{A}{B}\right) \quad (2)$$

Hence, the area A930 of the corner region 930 is equivalent to equation (3):

$$A930 = \tfrac{1}{2} \times (A-C-Y)(B-C-X) \quad (3)$$

After the total area (the area A930) of the failure region (the corner region 930) is learned, the loss rate α of the physiological signal value may be calculated as shown in equation (4):

$$\alpha = \frac{(A-C-Y)(B-C-X)}{2 \times (L \times W)} \quad (4)$$

The so-called "loss rate" is a percentage of the lost physiological signal value because a portion of the sensing region becomes the failure region after detachment.

After learning the "loss rate α", the compensation parameter ρ may be calculated as shown in equation (5):

$$\rho = \frac{1}{1-\alpha} \quad (5)$$

The compensation parameter ρ should be a numerical value greater than 1.

Assume that the physiological signal value detected by the signal processing device using the physiological signal sensor is PSV, the compensated physiological signal value is "PSV×ρ".

Figure 10:
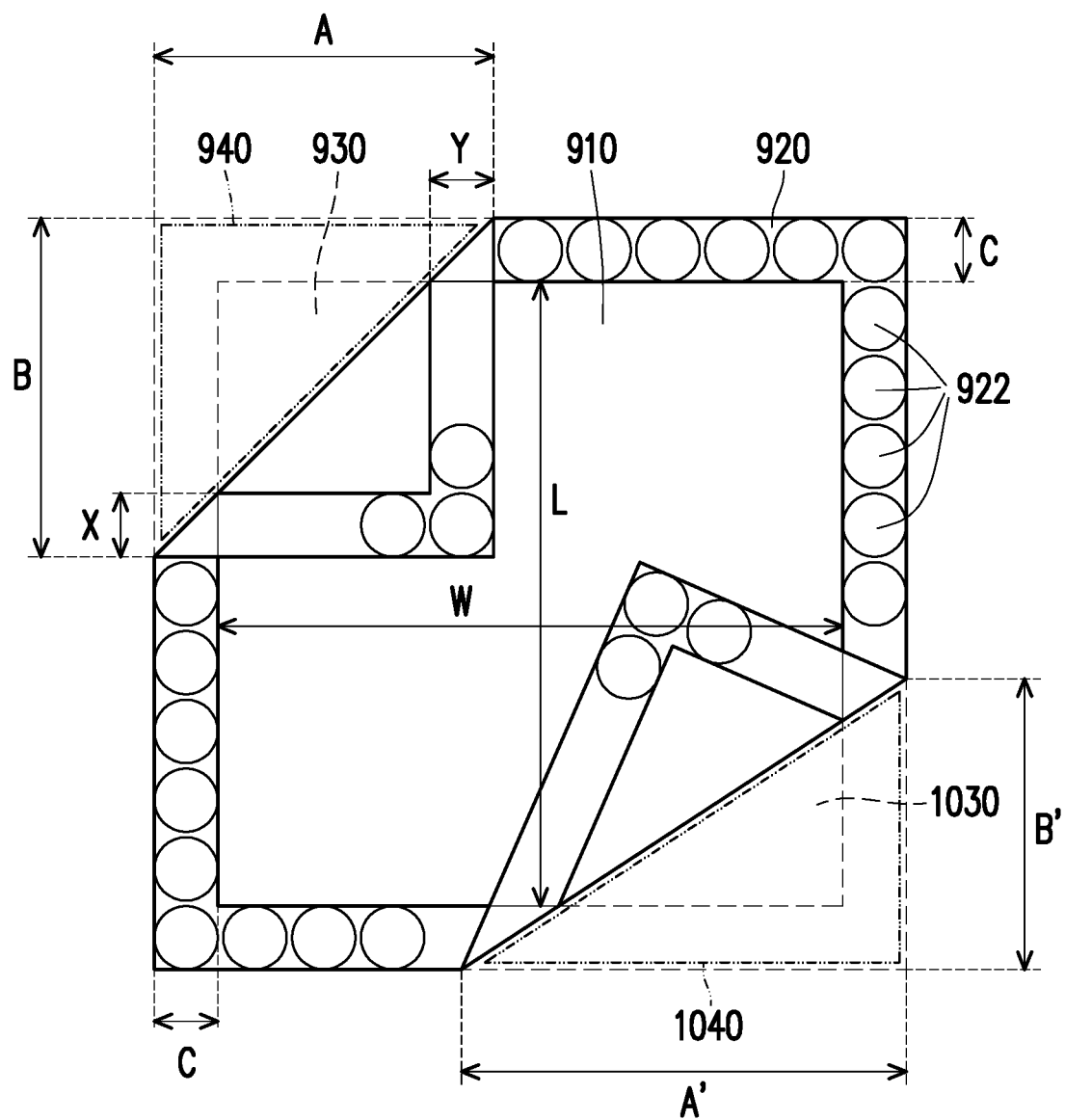
FIG. 10 is another schematic diagram of a sensing region and a failure region in a case where the sensing region is rectangular.

FIG. 10 is another schematic view of a sensing region 910 and a failure region, given that the sensing region 910 is rectangular. Similar to the settings provided in FIG. 9, the settings in FIG. 10 include two corner regions 930 and 1030, for instance. In FIG. 10, the failure region includes two corner regions 930 and 1030 in the sensing region 910. The signal processing device may obtain the boundary lengths A and B of the compensation region 940 including the corner region 930 and the boundary lengths A' and B' of the compensation region 1040 including the corner region 1030 according to the first compensation electrodes not connected to the object to be detected (some of the first compensation electrodes are shown) and the first compensation electrodes connected to the object to be detected. As such, the signal processing device may calculate an area A930 of the corner region 930 and an area A1030 of the corner region 1030 according to the boundary lengths A and B and the boundary lengths A' and B' and calculate the first compensation value corresponding to the physiological signal value according to the area A930, the area A1030, and the area of the sensing region 910. In detail, the total of the area A930 and the area A1030 may be expressed by using equation (6):

$$A930 + A1030 = \tfrac{1}{2} \times (A-C-Y)(B-C-X) + \tfrac{1}{2} \times (A'-C-Y)(B'-C-X) \quad (6)$$

The loss rate α can be expressed in equation (7):

$$\alpha = \frac{(A-C-Y)(B-C-X) + (A'-C-Y)(B'-C-X)}{2 \times (L \times W)} \quad (7)$$

The compensation parameter ρ is similar to that shown in equation (5), and the compensated physiological signal value ("PSV×ρ") may also be obtained through applying the calculation method depicted in FIG. 9.

Through the teachings shown in FIGS. 9 and 10, people who apply the embodiment may be aware that the failure region provided in the embodiment may include at least one to at most four detached corner regions, whereby the total area of the failure region may be calculated, and the compensated physiological signal value may then be calculated.

Figure 11:
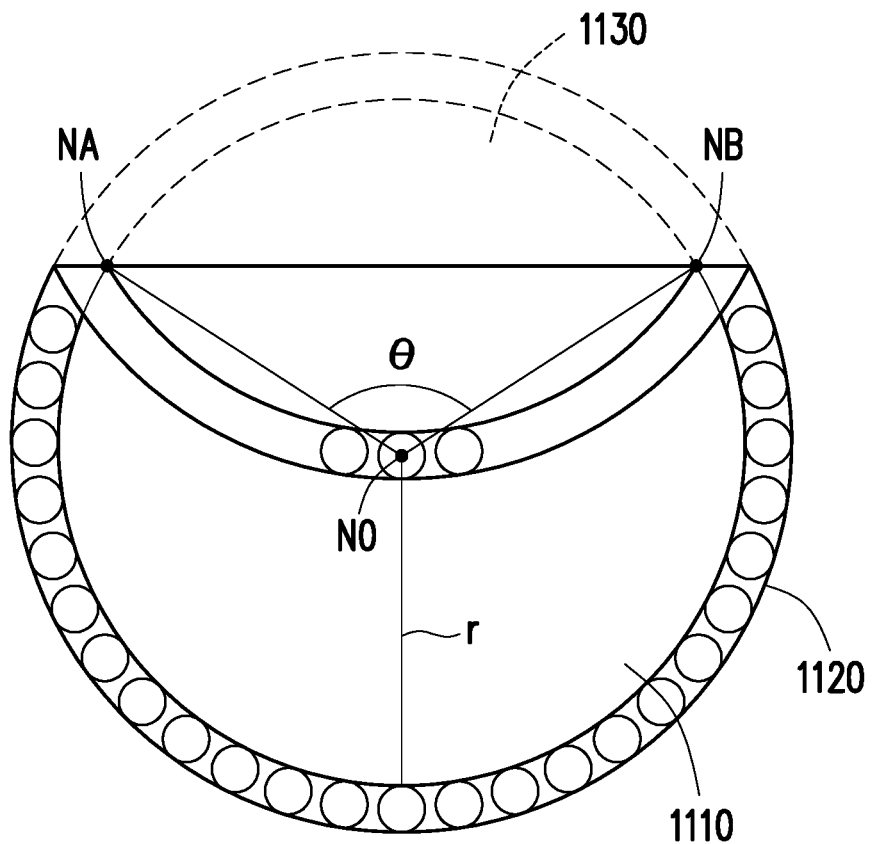
FIG. 11 is a schematic diagram of a sensing region and a failure region in a case where the sensing region is circular.

FIG. 11 is a schematic view of a sensing region 1110 and a failure region, given that the sensing region 1110 is circular. Here, the radius of the circular sensing region 1110 is set as r, and the center of the sensing region 1110 is expressed as NO. When the physiological sensor device is detached, the failure region includes at least one bow-shaped region 1130 in the sensing region 1110. For exemplary purposes, there is only one bow-shaped region 1130 according to the embodiment depicted in FIG. 11, and the area of one or a plurality of bow-shaped regions may be calculated by people applying the embodiment according to the description provided herein. The first compensation region 1120 includes a plurality of first compensation electrodes, and the signal processing device may calculate the area of the failure region according to failure locations NA and NB between the first compensation electrodes not connected to the object to be detected and the first compensation electrodes connected to the object to be detected.

After the failure locations NA and NB are learned, the signal processing device may learn an angle θ included by a line segment between the failure location NA and the center NO and a line segment between the failure location NB and the center NO according to the relationship between the center NO, the radius r, and the failure locations NA and NB. Thereby, an area A1130 of the bow-shaped region 1130 is the difference obtained by subtracting a triangular area formed by the failure locations NA, NB and the center NO from a fan-shaped area formed by the failure locations NA, NB and the center NO, as shown in equation (8):

$$A1130 = \quad (8)$$
$$(\theta/360)\pi r^2 - r^2 \times \sin(\theta/2)\cos(\theta/2) = (\theta/360)\pi r^2 - 1/2\, r^2 \sin\theta.$$

After the total area (the area A1130) of the failure region (the bow-shaped region 1130) is learned, the loss rate α of the physiological signal value may be calculated as shown in equation (9):

$$\alpha = \frac{(\theta/360)\pi r^2 - 1/2 r^2 \sin\theta}{\pi r^2} = \frac{\theta}{360} - \frac{\sin\theta}{2\pi} \quad (9)$$

The compensation parameter ρ is similar to that shown in equation (5), and the compensated physiological signal value ("PSV×ρ") may also be obtained through applying the calculation method depicted in FIG. 9 and FIG. 10.

Figure 12:
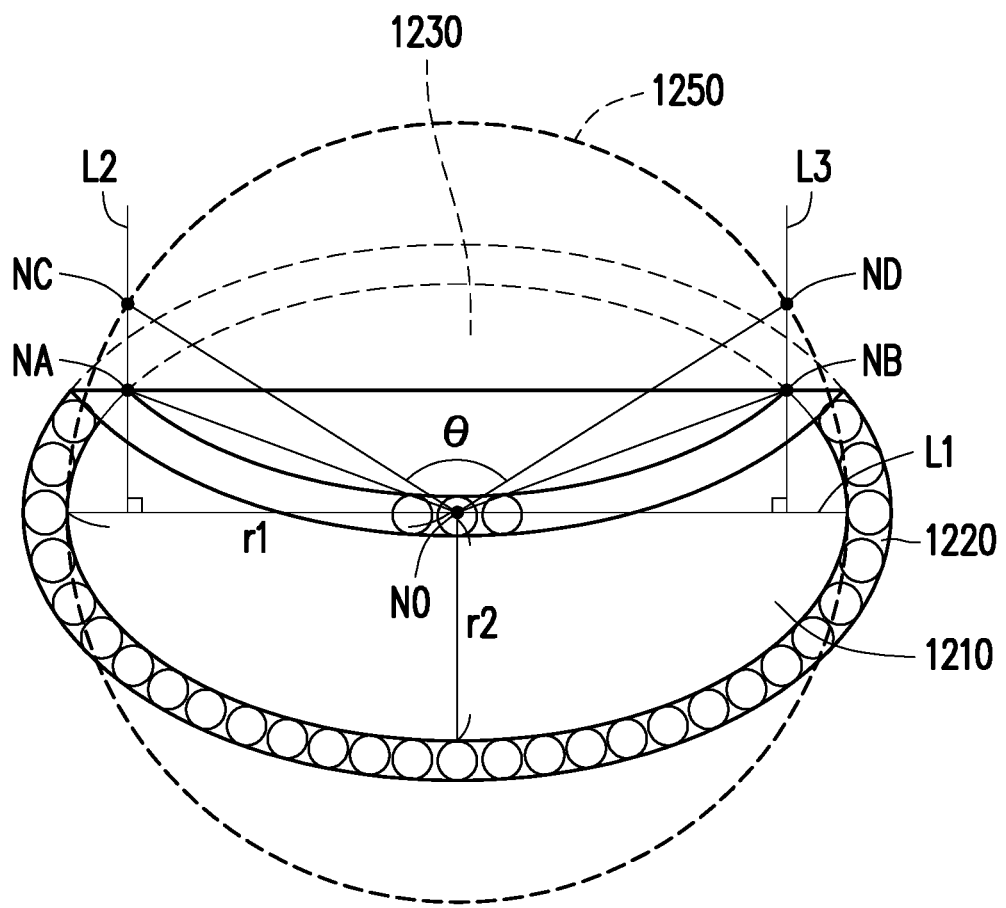
FIG. 12 is a schematic diagram of a sensing region and a failure region in a case where the sensing region is elliptical.

FIG. 12 is a schematic view of a sensing region 1210 and a failure region, given that the sensing region 1210 is elliptical. Here, the major axis of the elliptical sensing region 1210 is represented by r1, the minor axis of the elliptical sensing region 1210 is represented by r2, and the center of the sensing region 1210 is represented by NO. The center NO serves as the center of a virtual circle 1250 corresponding to the elliptical sensing region 1210, and the major axis r1 of the elliptical sensing region 1210 serves as the radius of the virtual circle 1250. When the physiological sensor device is detached, the failure region includes at least one bow-shaped region 1230 in the sensing region 1210. For exemplary purposes, there is only one bow-shaped region 1230 according to the embodiment depicted in FIG. 12, and the area of one or a plurality of bow-shaped regions may be calculated by people applying the embodiment according to the description provided herein. The first compensation region 1220 includes a plurality of first compensation electrodes, and the signal processing device may calculate the area of the failure region according to failure locations NA and NB between the first compensation electrodes not connected to the object to be detected and the first compensation electrodes connected to the object to be detected.

In detail, after the failure locations NA and NB are learned, locations NC and ND located on the virtual circle 1250 may be learned by using the line segments L2 and L3 perpendicular to a long axis L1 passing through the center NO; that is, the location NC and the failure location NA are located on the line segment L2, and the location ND and the failure location NB are located on the line segment L1. Here, the coordinates of the failure locations NA, the failure locations NB, the locations NC, and the locations ND are assumed to be (a1, a2), (b1, b2), (c1, c2), and (d1, d2). The signal processing device may learn an angle θ included by a line segment between the location NC and the center NO and a line segment between the location ND and the center NO by using the relationship between the center NO, the radius of the virtual circle 1250 (i.e., the major axis r1), and the locations NC and ND. An elliptical fan-shaped area Φ formed by the failure locations NA, NB and the center NO is as shown in equation (10):

$$\Phi = \left(\frac{r_1^2}{2}\right) \times \theta \tag{10}$$

The fan-shaped area formed by the locations NC, ND and the center NO in the virtual circle 1250 is $$\left(\frac{r_2}{r_1}\right) \times \Phi = \frac{1}{2 \times r_1 r_2 \times \theta}.$$

Hence, the angle θ may be learned from equations (11) and (12):

$$\cos\theta = \frac{c1 \times d1 + c2 \times d2}{\sqrt{c1^2 + c2^2} + \sqrt{d1^2 + d2^2}} = \frac{c1 \times d1 + c2 \times d2}{r1^2} \tag{11}$$

$$\theta = \cos^{-1}\left(\frac{c1 \times d1 + c2 \times d2}{r1^2}\right) \tag{12}$$

On the other hand, since c1=a1 and d1=b1, $$c2 = \frac{a2 \times r1}{r2} \text{ and } d2 = \frac{b2 \times r1}{r2},$$

thereby, the elliptical fan-shaped area Φ may be expressed as equation (13):

$$\Phi = \frac{1}{2r1 \times r2}\cos-1\left(\frac{a1 \times b1}{r1} + \frac{a2 \times b2}{r2}\right) \tag{13}$$

The triangular area formed by the failure locations NA, NB and the center NO is ½|a1×b2−a2×b1|.

As such, the area A1230 of the bow-shaped region 1230 is expressed in equation (14):

$$A1230 = \frac{1}{2r1 \times r2}\cos^{-1}\left(\frac{a1 \times b1}{r1} + \frac{a2 \times b2}{r2}\right) - \frac{1}{2}|a1 \times b2 - a2 \times b1| \tag{14}$$

The loss rate α can be expressed by equation (15):

$$\alpha = \tag{15}$$

$$\frac{1}{2\pi r1^2 \times r2^2}\cos^{-1}\left(\frac{a1 \times b1}{r1} + \frac{a2 \times b2}{r2}\right) - \frac{1}{2\pi r1 \times r2}|a1 \times b2 - a2 \times b1|$$

The compensation parameter ρ is similar to that shown in equation (5), and the compensated physiological signal value ("PSV×ρ") may also be obtained by applying the calculation method depicted in FIG. 9 to FIG. 11.

Figure 13:
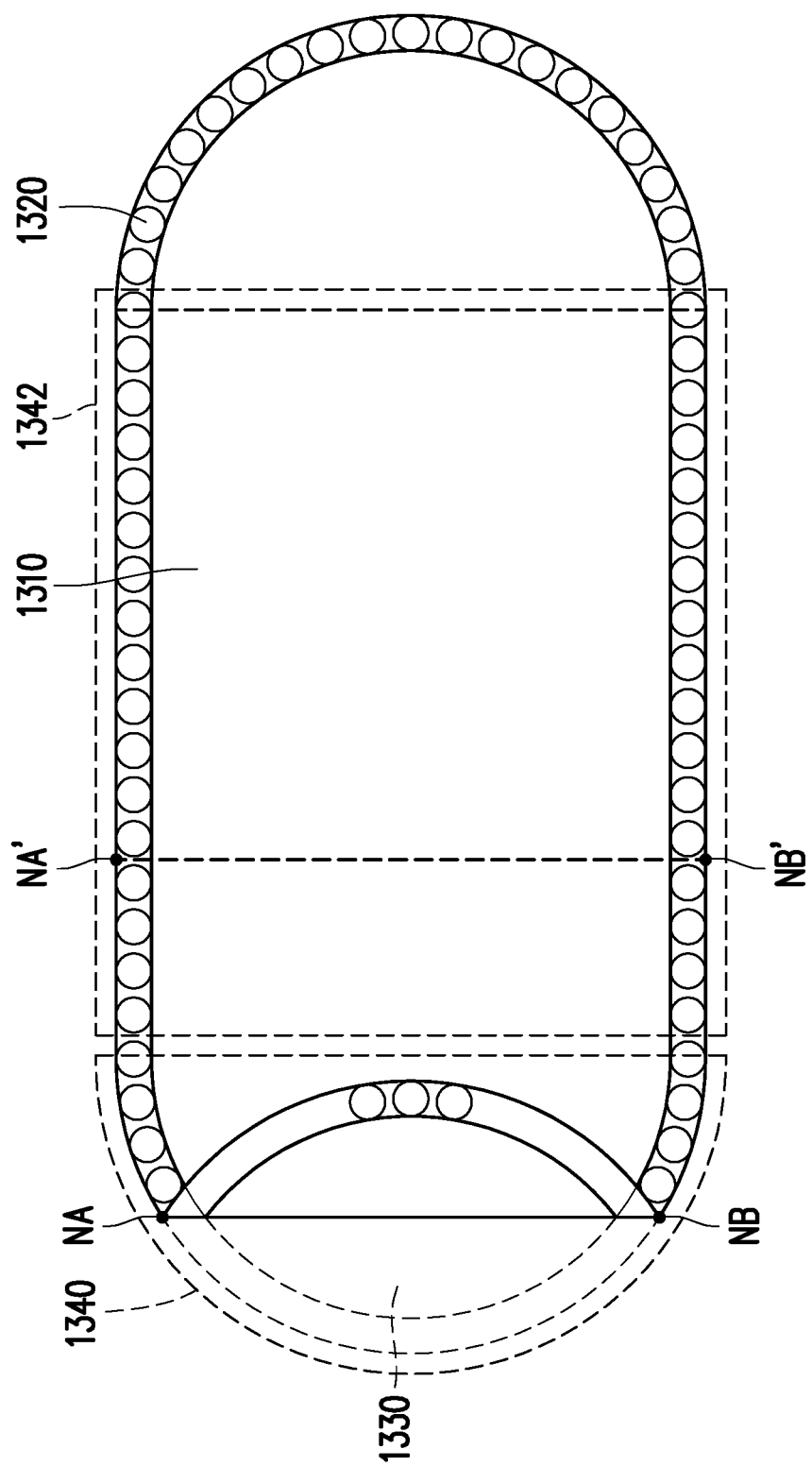
FIG. 13 is a schematic diagram of a sensing region and a failure region in a case where the sensing region is shaped as a rectangle combined with two semicircles.

The embodiments depicted in FIG. 9 to FIG. 12 are examples of calculating the area of the failure region based on the geometric shape. People applying the embodiment may combine the aforesaid geometric shapes to have more variety of the sensing regions. FIG. 13 is a schematic diagram of a sensing region 1310 and a failure region, given that the sensing region 1310 is shaped as a rectangle combined with two semicircles. The sensing region 1310 is an example showing the combination of two semicircles with one rectangle. Since the signal processing device may learn from the plurality of first compensation electrodes of the first compensation region 1320 the failure locations (e.g., the failure locations NA, NB and the failure locations NA', NB') between the first compensation electrodes not connected to the object to be detected (only some of the first compensation electrodes are depicted) and the first compensation electrodes connected to the object to be detected, the signal processing device can learn whether the failure locations NA, NB or the failure locations NA', NB' are located in the semicircular region 1340 or the rectangular region 1342 in the sensing region 1310. If the failure locations (e.g., the failure locations NA, NB) and the failure region (e.g., the bow-shaped region 1330) are merely located in the semicircular region 1340 in the sensing region 1310, the signal processing device can learn the area of the failure region by calculating the bow-shaped area in the manner depicted in FIG. 11. If the failure locations (e.g., the failure locations NA', NB') are located in the rectangular region 1342 in the sensing region 1310, indicating that the entire semicircular region 1340 is already detached, and the signal processing device may learn the area of the failure region according to the sum of an area of a trapezoidal region detached from the rectangular region plus the area of the entire semicircular region 1340.

Figure 14:
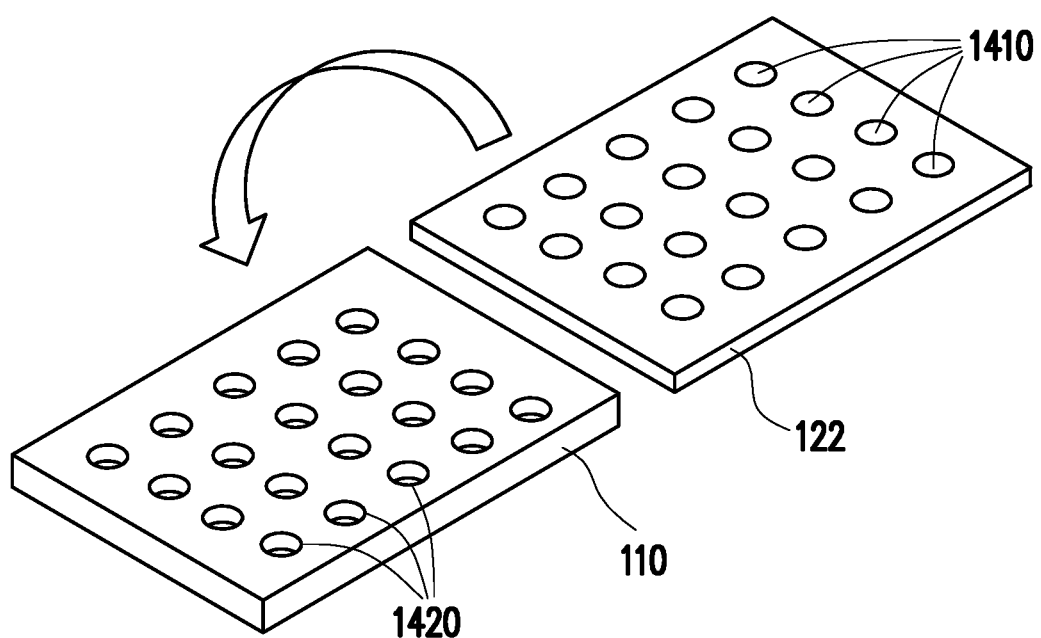
FIG. 14 is a schematic diagram of a physiological signal sensor and a second compensation sensor in a physiological sensor device.

FIG. 14 is a schematic diagram of the physiological signal sensor 110 and the second compensation sensor 122 in a physiological sensor device. According to the embodiment, the first compensation electrodes are disposed on the edge of the physiological signal sensor 110, and second compensation electrodes 1410 of the second compensation sensor 122 are arranged in a matrix on a sensing electrode in the physiological signal sensor 110. The sensing electrode of the physiological signal sensor 110 may include a plurality of vias 1420 in the embodiment, so that the second compensation electrodes 1410 may easily determine whether deformation occurs between the physiological signal sensor 110 and the object to be detected through the vias 1410. In other words, the signal processing device may determine whether deformation or wrinkle occurs between the physiological signal sensor 110 and the object to be detected according to the second compensation signal generated by each of the second compensation electrodes 1410 in the second compensation sensor 122 and compensate the physiological signal value sensed by the physiological signal sensor 110 according to the deformation or the wrinkle.

Figure 15:
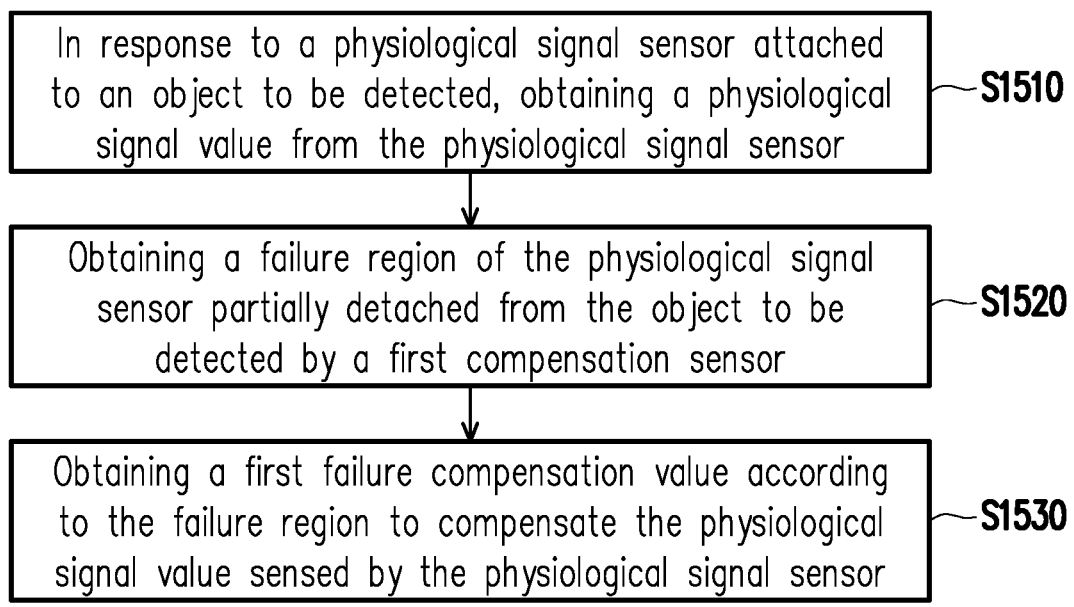
FIG. 15 is a flowchart of a correction method of a physiological signal according to an embodiment of the disclosure.

FIG. 15 is a flowchart of a correction method of a physiological signal according to an embodiment of the disclosure. The correction method is adapted to the physiological sensor device 100 mentioned in any of the previous embodiments and including the physiological signal sensor 110 and the first compensation sensor 120, and the first compensation sensor 120 is disposed on physiological signal sensor 110. With reference to FIG. 15, in step S1510, in response to the physiological signal sensor 110 being attached to object to be detected, the signal processing device 130 of the physiological sensor device 100 obtains the physiological signal value from the physiological signal sensor 110. In step S1520, the signal processing device 130 obtains through the first compensation sensor 120 the failure region of the physiological signal sensor 110 partially detached from the object to be detected. In step S1530, the signal processing device 130 obtains the first failure compensation value according to the failure region, so as to compensate the physiological signal value sensed by the physiological signal sensor 110. The detailed implementation of the aforesaid steps may be learned from the previous embodiments.

To sum up, embodiments of the disclosure provide a physiological sensor device, a physiological sensor system, a correction method of a physiological signal and a wearable device capable of detecting and feeding back a failure region of a physiological signal sensor partially detached between a sensing electrode and an object to be detected (e.g., a user's skin) and compensate and correct the physiological signal according to the failure region, so as to ensure the high accuracy of the physiological signal detected according to the embodiments of the disclosure. The physiological sensor device and the wearable device provided in one or more embodiments of the disclosure detect the failure region of the physiological signal sensor partially detached from the object to be detected with use of the first compensation sensor disposed on the edge of the sensing region in the physiological signal sensor and compensate the physiological signal value according to the ratio of the area of the failure region to the area of the sensing region in the physiological signal sensor, so as to calibrate the physiological signal value. Particularly, in the physiological sensor device provided in one or more embodiments of the disclosure, the plurality of compensation electrodes of the first compensation sensor are disposed on the edge of the sensing region in the physiological signal sensor. When the physiological signal sensor partially falls off, some of the compensation electrodes will not be connected to the object to be detected, and the other compensation electrodes are still connected to the object to be detected. As such, the form of the failure region (e.g., the corner region or the bow-shaped region) may be learned according to the predetermined shape of the sensing region in the physiological signal sensor (e.g., rectangular, circular, elliptical, or any other known predetermined composite shape), and the area of the failure region may be calculated using a plurality of failure locations between the compensation electrodes not connected to the object to be detected and the compensation electrodes connected to the object to be detected, so as to compensate the physiological signal value according to the area of the failure region and the area of the sensing region.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A physiological sensor device comprising:
a physiological signal sensor configured to be attached to an object to be detected to sense a physiological signal value;
a first compensation sensor disposed on the physiological signal sensor; and
a signal processing device coupled to the physiological signal sensor and the first compensation sensor, the signal processing device configured to obtain through the first compensation sensor a failure region of the physiological signal sensor partially detached from the object to be detected and to obtain a first failure compensation value according to the failure region, so as to compensate the physiological signal value sensed by the physiological signal sensor,
wherein the first compensation sensor comprises a plurality of first compensation electrodes, and the plurality of first compensation electrodes are disposed on an edge of a sensing region in the physiological signal sensor,
wherein the signal processing device calculates an area of the failure region according to a plurality of failure locations between the plurality of first compensation electrodes not connected to the object to be detected and the plurality of first compensation electrodes connected to the object to be detected.

2. The physiological sensor device as claimed in claim 1, wherein the sensing region in the physiological signal sensor is rectangular, and when the failure region comprises at least one corner region in the sensing region, the signal processing device obtains a boundary length of the at least one corner region according to the plurality of failure locations, calculates an area of the at least one corner region according to the boundary length, and calculates the first failure compensation value according to the area of the at least one corner region and an area of the sensing region.

3. The physiological sensor device as claimed in claim 1, wherein the sensing region in the physiological signal sensor is circular or elliptical, and when the failure region comprises at least one bow-shaped region in the sensing region, the signal processing device calculates an area of the at least one bow-shaped region according to the plurality of failure locations and a center of the sensing region and calculates the first failure compensation value according to the area of the at least one bow-shaped region and an area of the sensing region.

4. The physiological sensor device as claimed in claim 1, further comprising:
a reference electrode attached to the object to be detected to sense a reference signal value, the reference signal value serving as a comparison basis for calibrating a sensing electrode in the physiological signal sensor.

5. The physiological sensor device as claimed in claim 1, further comprising:
a second compensation sensor comprising a plurality of second compensation electrodes, the plurality of second compensation electrodes being arranged in a matrix on a sensing electrode in the physiological signal sensor,
wherein the signal processing device determines whether deformation or wrinkle occurs between the physiological signal sensor and the object to be detected according to a second compensation signal generated by the second compensation sensor and compensate the physiological signal value sensed by the physiological signal sensor according to the deformation or the wrinkle.

6. The physiological sensor device as claimed in claim 1, further comprising a fixing member configured to fix the physiological signal sensor and the first compensation sensor.

7. A correction method of a physiological signal adapted to a physiological sensor device comprising a physiological signal sensor and a first compensation sensor, the first compensation sensor being disposed on the physiological signal sensor, wherein the correction method comprises:
in response to the physiological signal sensor being attached to an object to be detected, obtaining a physiological signal value from the physiological signal sensor;
obtaining a failure region of the physiological signal sensor partially detached from the object to be detected by the first compensation sensor; and
obtaining a first failure compensation value according to the failure region to compensate the physiological signal value sensed by the physiological signal sensor,
wherein the first compensation sensor comprises a plurality of first compensation electrodes, and the plurality of first compensation electrodes are disposed on an edge of a sensing region in the physiological signal sensor,
wherein the step of obtaining the failure region of the physiological signal sensor partially detached from the object to be detected by the first compensation sensor comprising:
calculating an area of the failure region according to a plurality of failure locations between the plurality of first compensation electrodes not connected to the object to be detected and the plurality of first compensation electrodes connected to the object to be detected.

8. The correction method as claimed in claim 7, the step of calculating the failure region comprising:
when a sensing region in the physiological signal sensor is rectangular, and when the failure region comprises at least one corner region in the sensing region, obtaining a boundary length of the at least one corner region according to the plurality of failure locations and calculating an area of the at least one corner region according to the boundary length.

9. The correction method as claimed in claim 7, the step of calculating the failure region comprising:
when the sensing region in the physiological signal sensor is circular or elliptical, and when the failure region comprises at least one bow-shaped region in the sensing region, calculating an area of the at least one bow-shaped region according to the plurality of failure locations and a center of the sensing region.

10. The correction method as claimed in claim 7, the step of obtaining the first failure compensation value according to the failure region comprising:
calculating the first failure compensation value according to an area of the failure region and an area of the sensing region.

11. The correction method as claimed in claim 7, wherein the physiological sensor device further comprises a second compensation sensor comprising a plurality of second compensation electrodes arranged in a matrix on a sensing electrode of physiological signal sensor;
wherein the correction method further comprises:
determining whether deformation or wrinkle occurs between the physiological signal sensor and the object to be detected according to a second compensation signal generated by the second compensation sensor; and
compensating the physiological signal value sensed by the physiological signal sensor according to the deformation or the wrinkle.

12. A physiological sensor system comprising:
a host device; and
a physiological sensor device communicating with the host device, wherein the host device configured to obtain a compensated physiological signal value provided by the physiological sensor device to perform data computation and to present a physiological signal value after the data computation,
wherein the physiological sensor device comprises:
a physiological signal sensor configured to be attached to an object to be detected to sense a physiological signal value;
a first compensation sensor disposed on the physiological signal sensor; and
a signal processing device coupled to the physiological signal sensor and the first compensation sensor, the signal processing device configured to obtain through the first compensation sensor a failure region of the physiological signal sensor partially detached from the object to be detected and to obtain a first failure compensation value according to the failure region, so as to compensate the physiological signal value sensed by the physiological signal sensor,
wherein the first compensation sensor comprises a plurality of first compensation electrodes, and the plurality of first compensation electrodes are disposed on an edge of a sensing region in the physiological signal sensor,
wherein the signal processing device calculates an area of the failure region according to a plurality of failure locations between the plurality of first compensation electrodes not connected to the object to be detected and the plurality of first compensation electrodes connected to the object to be detected.

* * * * *